United States Patent [19]

Ito et al.

[11] Patent Number: 4,898,985
[45] Date of Patent: Feb. 6, 1990

[54] PROCESS FOR PREPARING 3,5,5-TRIMETHYLCYCLOHEXA-2-EN-1,4-DIONE

[75] Inventors: Nobuhiko Ito; Kimio Kinoshita; Kiyonori Suzuki; Takeaki Eto, all of Chiba, Japan

[73] Assignee: Soda Aromatic Company, Limited, Japan

[21] Appl. No.: 254,212

[22] Filed: Oct. 6, 1988

[30] Foreign Application Priority Data

Oct. 6, 1987 [JP] Japan .................................. 62-250625

[51] Int. Cl.$^4$ ............................................ C07C 45/34
[52] U.S. Cl. .................................................. 568/344
[58] Field of Search ........................ 568/344, 360, 389

[56] References Cited

U.S. PATENT DOCUMENTS

| | | | |
|---|---|---|---|
| 3,944,620 | 3/1976 | Becker et al. | 568/344 |
| 4,026,947 | 5/1977 | Costantini et al. | 568/344 |
| 4,046,813 | 9/1977 | Brenner | 568/344 |
| 4,092,361 | 5/1978 | Costantini et al. | 568/344 |
| 4,393,244 | 7/1983 | Bhaduri et al. | 568/360 |
| 4,568,769 | 2/1986 | Yashima et al. | 568/360 |

FOREIGN PATENT DOCUMENTS

| | | | |
|---|---|---|---|
| 1261510 | 9/1965 | Fed. Rep. of Germany | 568/344 |
| 2335486 | 7/1977 | France | 568/344 |
| 63-122644 | 5/1988 | Japan | 568/344 |

*Primary Examiner*—James H. Reamer
*Attorney, Agent, or Firm*—Scully, Scott, Murphy & Presser

[57] ABSTRACT

3,5,5-Trimethylcyclohexa-2-en-1,4-diones is prepared by oxidizing 3,5,5-trimethylcyclohexa-3-en-one with molecular oxygen or a molecular oxygen-containing gas in the presence of an organic base and an organometallic complex catalyst comprising manganese, iron, cobalt or copper atom and at least four nitrogen atoms coordination-bonded thereto.

10 Claims, No Drawings

PROCESS FOR PREPARING 3,5,5-TRIMETHYLCYCLOHEXA-2-EN-1,4-DIONE

BACKGROUND OF THE INVENTION

The present invention relates to a process for preparing 3,5,5-trimethylcyclohexa-2-en-1,4-dione which per se is highly valued as a perfume for foods, fragrances and tobaccos and is useful as an intermediate for the production of drugs and perfumes, e.g. carotnoids and vitamin E.

Heretofore, various processes have been proposed for preparing 3,5,5-trimethylcyclohexa-2-en-1,4-dione. According to the process disclosed in West German Pat. No. 2,365,546, 3,5,5-trimethylcyclohexa-2-en-1-one (hereinafter referred to as "α-isophorone") is oxidized with chromium oxide in a mixed solvent of acetic acid and acetic anhydride to thereby prepare 3,5,5-trimethylcyclohexa-2-en-1,4-dione in a yield of about 50% relative to α-isophorone. This process is disadvantageous in that the percentage conversion and yield are low; it is required to use a large excess of chromium oxide relative to α-isophorone, thus causing the danger of explosion; the production cost is high; and much labor is required for the disposal of chromium waste. According to West German Pat. No. 2,457,158, α-isophorone is oxidized in vapor phase in the presence of a vanadium catalyst to thereby prepare 3,5,5-trimethylcyclohexa-2-en-1,4-dione in a yield of about 30% relative to α-isophorone. This process is disadvantageous in that the percentage conversion and yield are low and 5,5-dimethyl-3-formylcyclohexa-2-en-1,4-dione is by-produced in about the same amount as 3,5,5-trimethylcyclohexa-2-en-1,4-dione. According to West German Pat. No. 2,459,148, α-isophorone is oxidized in liquid phase in the presence of an acetylacetonato iron or cobalt catalyst or a rhodium (I) tristriphenylphosphine chloride catalyst to thereby prepare 3,5,5-trimethylcyclohexa-2-en-1,4-dione in an yield of about 30% relative to α-isophorone. This process is disadvantageous in that selectivity and yield are poor. In Japanese Patent Laid-Open No. 191645/1986, 3,5,5-trimethylcyclohexa-2-en-1,4-dione is prepared in a yield of about 50% by oxidized α-isophorone in the presence of an alkali metal or an aromatic amine and phosphomolybdic acid or silicomolybdic acid. This process is disadvantageous in that the percentage conversion and yield are low and α-isophorone, which is difficult to be separated from 3,5,5-trimethylcyclohexa-2-en-1,4-dione, is contained in about the same amount in the reaction product. In French Pat. No. 2,254,730, 3,5,5-trimethylcyclohexa-3-en-1-one (hereinafter referred to as "β-isophorone") is oxidized in an alcohol solvent in the presence of a tertiary amine and copper (II) salt of pyridine to thereby prepare 3,5,5-trimethylcyclohexa-2-en-1,4-dione in a yield of about 30% relative to β-isophorone. This process is disadvantageous in that the yield is low and a polymer of β-isophorone is byproduced in a fairly large amount. Further, in West German Pat. No. 2,457,157, α-isophorone is oxidized over a period of about 35 hours in the presence of an acetylacetonate complex catalyst which is derived from a transition metal such as vanadium, chromium, copper, manganese, iron, cobalt, or nickel to thereby prepare 3,5,5-trimethylcyclohexa-2-en-1,4-dione in a maximum yield of 55% relative to β-isophorone. This process is disadvantageous in that the reaction time is long and yield is low.

It is the object to the present invention to provide a process for preparing 3,5,5-trimethylcyclohexa-2-en-1,4-dione industrially advantageously which process is free of the above-mentioned disadvantages or drawbacks of the prior art.

SUMMARY OF THE INVENTION

The present invention resides in the process for preparing 3,5,5-trimethylcyclohexa-2-en-1,4-dione in which process 3,5,5-trimethylcyclohexa-3-en-1-one is oxidized with molecular oxygen or a molecular oxygen-containing gas in the presence of an organic base and an organometallic complex catalyst comprising manganese, iron, cobalt or copper atom and at least four nitrogen atoms coordination-bonded thereto.

According to such process of the present invention, the polymerization and side reaction of β-isophorone are supressed as compared with the conventional processes and 3,5,5-trimethylcyclohexa-2-en-1,4-dione can be prepared industrially advantageously and in high yield without formation of any by-product difficult to be separated from the desired product.

DETAILED DESCRIPTION OF THE INVENTION

The β-isophorone used in the present invention can be prepared, for example, by a process (U.S. Pat. No. 3,385,902) wherein α-isophorone is distilled in the presence of p-toluenesulfonic acid. As the organometallic complex catalyst used in the invention there may be used substantially any compound if only at least four nitrogen atoms are coordination-bonded to manganese, iron, cobalt or copper atom.

Various complexes are known as examples of such organo-metallic complex. Particularly, those having complex structures called porphyrin complex and phthalocyanine complex are preferred, the former exhibiting specially outstanding effects in the process of the present invention.

As well known, porphyrin complex has a basic structure represented by the following formula (I):

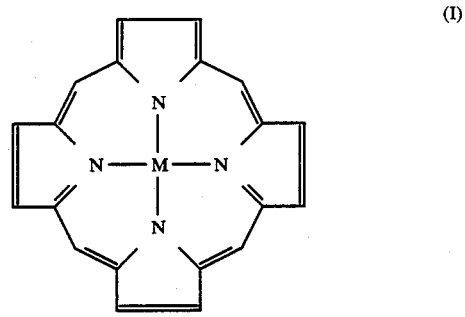

(I)

wherein M represents a metal atom. Used in the present invention is one wherein M is manganese, cobalt, iron or copper.

The reason why the porphyrine complexes of the formula (I) is particularly preferred is presumed to be that the electron transfer between metal ions and tetrapyrrole is easy because there is contained a large electron system exhibiting aromatic properties as tetrapyrrole.

As long as there is the basic structure shown in the formula (I), substantially any substituent groups may be bonded thereto, which can be suitably selected, for example, taking into account whether the porphyrin material for forming a complex with metal M is easily available or not. For explanation on substituent groups of high utility, there is given the following general formula (I') showing a porphyrin complex with substituent groups in the formula (I):

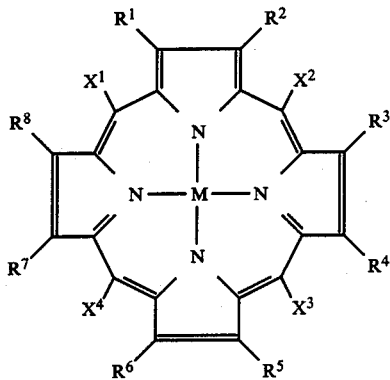
(I')

Preferably, in the above formula, $X^1$, $X^2$, $X^3$ and $X^4$, which may be the same or different, are each hydrogen, $C_1$-$C_4$ alkyl, $C_1$-$C_4$ alkoxy, or phenyl, which phenyl may be substituted with one to five halogen atoms, $C_1$-$C_4$ alkyl, $C_1$-$C_4$ alkoxy, or phenyl; $R^1$, $R^2$, $R^3$, $R^4$, $R^5$, $R^6$, $R^7$ and $R^8$ are each hydrogen atom, $C_1$-$C_4$ alkyl, $C_1$-$C_4$ alkoxy, halogen atom, $C_1$-$C_4$ alkylamino, or nitro; and M is manganese, cobalt, iron, or copper.

Phthalocyanine complex, as well known, has a basic structure represented by the following formula (II):

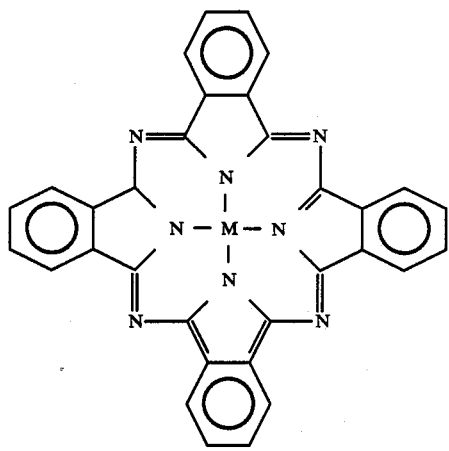
(II)

Substituent groups bonded to such basic structure of phthalocyanine complex are not specially limited as in the case of porphyrin complex, but for illustration of those of high utility there can be given the following general formula (II'):

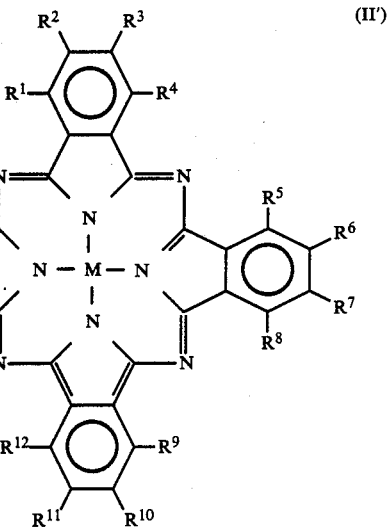
(II')

Preferably, in the above formula, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are each hydrogen atom, $C_1$-$C_4$ alkyl, $C_1$-$C_4$ alkoxy, halogen atom, or $C_1$-$C_4$ alkylamino; and M is manganese, iron, cobalt, or copper.

In these organometallic complexes, it is presumed that the four nitrogen atoms are coordination bonded to the metal in the form of a quadrilateral in plane or in a form similar thereto. Where required, as the fifth and sixth ligands there may be used various compounds having coordination ability. Examples are gases such as oxygen molecule, oxygen atom, carbon monoxide and nitrogen monoxide; halogen ions such as chlorine bromine, fluorine and iodine; nucleophiles such as methylate, ethylate, phenolate, isothiocyanate, azide, hydroxide, cyanide, perfluorate, methane thiolate and acetate; organic bases such as pyridine and imidazole; ethers such as tetrahydrofuran and 1,4-dioxane; and acetonitrile.

Examples of $X^1$, $X^2$, $X^3$, $X^4$, $R^1$, $R^2$, $R^3$, $R^4$, $R^5$, $R^6$, $R^7$, $R^8$ and M in the general formula (I') are shown in Table-1 together with compound names, while examples of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and M are shown in Table-2 together with compound names. Most of them are available easily.

TABLE 1

| No. | R¹ | R² | R³ | R⁴ | R⁵ | R⁶ | R⁷ | R⁸ | X¹ | X² | X³ | X⁴ | M | Name |
|---|---|---|---|---|---|---|---|---|---|---|---|---|---|---|
| 1 | H | H | H | H | H | H | H | H | H | H | H | H | Mn | PMn |
| 2 | " | " | " | " | " | " | " | " | " | " | " | " | MnCl | Chloro PMn |
| 3 | " | " | " | " | " | " | " | " | " | " | " | " | Co | PCo |
| 4 | " | " | " | " | " | " | " | " | " | " | " | " | Fe | PFe |
| 5 | " | " | " | " | " | " | " | " | " | " | " | " | FeCl | Chloro PFe |
| 6 | Et | Et | Et | Et | Et | Et | Et | Et | H | H | H | H | Mn | 2,3,7,8,12,13,17,18-Octaethyl |
| 7 | " | " | " | " | " | " | " | " | " | " | " | " | MnCl | Chloro-2,3,7,8,12,13,17,18-Octaethyl PMn |
| 8 | " | " | " | " | " | " | " | " | " | " | " | " | Co | 2,3,7,8,12,13,17,18-Octaethyl PCo, |
| 9 | " | " | " | " | " | " | " | " | " | " | " | " | CoCl | Chloro-2,3,7,8,12,13,17,18-Octaethyl PCo |
| 10 | " | " | " | " | " | " | " | " | " | " | " | " | CoClO₄ | Perchloro-2,3,7,8,12,13,17,18-Octaethyl PCo |
| 11 | " | " | " | " | " | " | " | " | " | " | " | " | CoBr | Bromo-2,3,7,8,12,13,17,18-Octaethyl PCo |
| 12 | " | " | " | " | " | " | " | " | " | " | " | " | Fe | 2,3,7,8,12,13,17,18-Octaethyl PCo |
| 13 | " | " | " | " | " | " | " | " | " | " | " | " | FeCl | Chloro-2,3,7,8,12,13,17,18-Octaethyl PFe |
| 14 | " | " | " | " | " | " | " | " | " | " | " | " | FeClO₄ | Perchloro-2,3,7,8,12,13,17,18-Octaethyl PFe |
| 15 | " | " | " | " | " | " | " | " | " | " | " | " | FeOAc | Acethyloxy-2,3,7,8,12,13,17,18-Octaethyl PFe |
| 16 | Et | Et | Et | Et | Et | Et | Et | Et | Me | Me | Me | H | Mn | 2,3,7,8,12,13,17,18-Octaethyl-5,15-dimethyl PMn |
| 17 | " | " | " | " | " | " | " | " | " | " | " | " | MnCl | Chloro-2,3,7,8,12,13,17,18-Octaethyl-5,15-dimethyl PMn |
| 18 | " | " | " | " | " | " | " | " | Me | " | " | " | Mn | 2,3,7,8,12,13,17,18-Octaethyl-5-methyl PMn |
| 19 | " | " | " | " | " | " | " | " | " | " | " | " | MnCl | Chloro-2,3,7,8,12,13,17,18-Octaethyl-5-methyl PMn |
| 20 | " | " | " | " | " | " | " | " | Ph | " | " | " | Mn | 2,3,7,8,12,13,17,18-Octaethyl-5-phenyl PMn |
| 21 | " | " | " | " | " | " | " | " | " | " | " | " | MnCl | Chloro-2,3,7,8,12,13,17,18-Octaethyl-5-phenyl-PMn |
| 22 | Me | " | " | " | " | " | " | " | H | H | H | H | Mn | 2,3,7,8,12,13,17,18-Octaethyl PMn |
| 23 | " | " | " | " | " | " | " | " | " | " | " | " | MnCl | Chloro-2,3,7,8,12,13,17,18-Octaethyl PMn |
| 24 | " | " | " | " | " | " | " | " | Et | Et | Et | Et | Mn | 5,10,15,20-Tetrabutyl PMn |
| 25 | " | " | " | " | " | " | " | " | Bu | Bu | Bu | Bu | Mn | 5,10,15,20-Tetrabutyl PMn |
| 26 | Br | " | Br | " | Br | " | Br | " | Ph | Ph | Ph | Ph | Mn | 2,7,12,17,-Tetrabromo-5,10,15,20-tetraphenyl PMn |
| 27 | Et | Me | Et | Me | Et | Me | Et | Me | H | OMe | H | H | Mn | 2,7,12,17-Tetraethyl-5-methoxy-3,8,13,18-tetramethyl PMn |
| 28 | " | " | " | " | " | " | " | " | " | H | " | " | Mn | 2,7,12,17-Tetraethyl-3,8,13,18-tetramethyl PMn |
| 29 | " | " | " | " | " | " | " | " | " | " | " | " | MnNO₃ | Nitrato-2,7,12,17-tetraethyl-3,8,13,18-tetramethyl PMn |
| 30 | " | " | " | " | " | " | " | " | " | " | " | " | MnCl | Chloro-2,7,12,17-tetraethyl-3,8,13,18-tetramethyl PMn |
| 31 | " | " | " | " | " | " | " | " | " | " | " | " | MnBr | Bromo-2,7,12,17-tetraethyl-3,8,13,18-tetramethyl PMn |
| 32 | " | " | " | " | " | " | " | " | " | " | " | " | MnI | Iodo-2,7,12,17-tetraethyl-3,8,13,18-tetramethyl PMn |
| 33 | " | H | Et | Me | " | H | Et | Me | " | " | " | " | Mn | 2,7,12,18-Tetraethyl-3,8,13,17-tetramethyl PMn |
| 34 | H | Me | H | Me | H | Me | H | Me | " | " | " | " | MnCl | Chloro-5,10,15,20-tetrapropyl PMn |
| 35 | Et | Me | " | Me | Et | " | Et | Et | Pr | Pr | Pr | Pr | Mn | 2,7,13,18-Tetraethyl-3,8,12,17-tetramethyl PMn |
| 36 | " | " | Me | Et | " | Me | Et | " | H | H | H | H | Mn | 2,8,12,18-Tetraethyl-3,7,13,17-tetramethyl PMn |
| 37 | " | " | Et | Me | " | Et | " | Me | " | NO₂ | " | " | Mn | 2,7,12,17-tetraethyl-3,8,13,18-tetramethyl-5-nitro PMn |
| 38 | " | Me | Me | Et | Me | Me | Me | Et | " | ⌬ | " | " | Mn | 2,8,12,18-Tetraethyl-3,7,13,17-tetramethyl-10-phenyl PMn |
| 39 | Me | Et | Et | Me | Et | Et | Et | Me | ⌬ | H | H | H | Mn | 3,7,13,17-Tetraethyl-2,8,12,18-tetramethyl-5-phenyl PMn |
| 40 | H | H | H | H | H | H | H | H | F—⌬ | F—⌬ | F—⌬ | F—⌬ | MnF | Fluoro-5,10,15,20-tetrakis (4-fluorophenyl) PMn |
| 41 | " | " | " | " | " | " | " | " | " | " | " | " | MnCl | Chloro-5,10,15,20-tetrakis (4-fluorophenyl) PMn |

TABLE 1-continued

| No. | R¹ | R² | R³ | R⁴ | R⁵ | R⁶ | R⁷ | R⁸ | X¹ | X² | X³ | X⁴ | M | Name |
|---|---|---|---|---|---|---|---|---|---|---|---|---|---|---|
| 42 | " | " | " | " | " | " | " | " | Et | Et | Et | Et | MnI | Iodo-5,10,15,20-tetrakis (4-fluorophenyl) PMn |
| 43 | " | " | " | " | " | " | " | " | OMe | OMe | OMe | OMe | MnOAC | Acethyloxy-5,10,15,20-tetrakis (4-methoxyphenyl) PMn |
| 44 | " | " | " | " | " | " | " | " | ⌬ | ⌬ | ⌬ | ⌬ | MnCl | Chloro-5,10,15,20-tetrakis (2-methylphenyl) PMn |
| 45 | " | " | " | " | " | " | " | " | ⌬ | ⌬ | ⌬ | ⌬ | MnCl | Chloro-5,10,15,20-tetrakis (3-methylphenyl) PMn |
| 46 | " | " | " | " | " | " | " | " | ⌬ | ⌬ | ⌬ | ⌬ | MnCl | Chloro-5,10,15,20-tetrakis (4-methylphenyl) PMn |
| 47 | " | " | " | " | " | " | " | " | " | " | " | " | MnBr | Bromo-5,10,15,20-tetrakis (4-methylphenyl) PMn |
| 48 | " | " | " | " | " | " | " | " | " | " | " | " | MnF | Fluoro-5,10,15,20-tetrakis (4-methylphenyl) PMn |
| 49 | H | H | H | H | H | H | H | H | ⌬ | ⌬ | ⌬ | ⌬ | MnI | Iodo-5,10,15,20-tetrakis (4-methylphenyl) PMn |
| 50 | " | " | " | " | " | " | " | " | " | " | " | " | MnN₃ | Azide-5,10,15,20-tetrakis (4-methylphenyl) PMn |
| 51 | " | " | " | " | " | " | " | " | NO₂⌬ | NO₂⌬ | NO₂⌬ | NO₂⌬ | Mn | 5,10,15,20-Tetrakis (4-nitrophenyl) PMn |
| 52 | Me | H | Me | H | Me | H | Me | H | H | H | H | H | Mn | 2,7,12,17-Tetramethyl PMn |
| 53 | H | H | H | H | H | H | H | H | Me | Me | Me | Me | Mn | 5,10,15,20-Tetramethyl PMn |
| 54 | " | " | " | " | " | " | " | " | ⌬ | ⌬ | ⌬ | ⌬ | MnBr | Bromo-5,10,15,20-tetraphenyl PMn |
| 55 | " | " | " | " | " | " | " | " | " | " | " | " | MnCl | Chloro-5,10,15,20-tetraphenyl PMn |
| 56 | " | " | " | " | " | " | " | " | " | " | " | " | MnF | Fluoro-5,10,15,20-tetraphenyl PMn |
| 57 | " | " | " | " | " | " | " | " | " | " | " | " | MnI | Iodo-5,10,15,20-tetraphenyl PMn |
| 58 | " | " | " | " | " | " | " | " | " | " | " | " | MnNOCl | Chloronitrosyl-5,10,15,20-tetraphenyl PMn |
| 59 | " | " | " | " | " | " | " | " | " | " | " | " | Mn | 5,10,15,20-Tetraphenyl PMn |
| 60 | " | " | " | " | " | " | " | " | " | " | " | " | MnNO | Nitrosyl-5,10,15,20-tetraphenyl PMn |
| 61 | " | " | " | " | " | " | " | " | " | " | " | " | MnN₃ | Azide-5,10,15,20-tetraphenyl PMn |
| 62 | " | " | " | " | " | " | " | " | " | " | " | " | Co | 5,10,15,20-Tetraphenyl PCo |
| 63 | " | " | " | " | " | " | " | " | " | " | " | " | CoCl | Chloro-5,10,15,20-tetraphenyl PCo |
| 64 | " | " | " | " | " | " | " | " | " | " | " | " | CoBr | Bromo-5,10,15,20-tetraphenyl PMn |

TABLE 1-continued

| No. | R¹ | R² | R³ | R⁴ | R⁵ | R⁶ | R⁷ | R⁸ | X¹ | X² | X³ | X⁴ | M | Name |
|---|---|---|---|---|---|---|---|---|---|---|---|---|---|---|
| 65 | H | H | H | H | H | H | H | H | Ph | Ph | Ph | Ph | Fe | 5,10,15,20-Tetraphenyl PFe |
| 66 | " | " | " | " | " | " | " | " | " | " | " | " | FeCl | Chloro-5,10,15,20-tetraphenyl PFe |
| 67 | " | " | " | " | " | " | " | " | " | " | " | " | FeBr | Bromo-5,10,15,20-tetraphenyl PFe |
| 68 | " | " | " | " | " | " | " | " | " | " | " | " | MnOAc | Acetyloxy-5,10,15,20-tetraphenyl PMn |
| 69 | " | " | " | " | " | " | " | " | " | " | " | " | MnNOAc | Acetylnitrosyl-5,10,15,20-tetraphenyl PMn |
| 70 | " | " | " | " | " | " | " | " | " | " | " | " | Mn(NO)(OAc) | Acetyloxy-nitrosyl-5,10,15,20-tetraphenyl PMn |
| 71 | " | " | " | " | " | " | " | " | F-Ph | F-Ph | F-Ph | F-Ph | MnOAc | Acetyloxy-5,10,15,20-tetraphenyl PMn |
| 72 | " | " | " | " | " | " | " | " | (OMe)₃-Ph | " | " | " | MnOAc | Acetyloxy-5,10,15,20-tetrakis (2,4,6-trimethoxyphenyl) PMn |
| 73 | " | " | " | " | " | " | " | " | Ph₃-Ph | " | " | " | MnOAc | Acetyloxy-5,10,15,20-tetrakis (2,4,6-triphenyl) PMn |
| 74 | " | " | " | " | " | " | " | " | Ph | Ph | Ph | Ph | MnClO₄ | Perchloro-5,10,15,20-tetrakis (2,4,6-triphenyl) PMn |
| 75 | " | " | " | " | " | " | " | " | Mesityl | Mesityl | Mesityl | Mesityl | MnCl | Chloro-5,10,15,20-tetramesityl PMn |
| 76 | " | " | " | " | " | " | " | " | " | " | " | " | MnOAc | Acetyloxy-5,10,15,20-tetramesityl PMn |

Note
PMn = Porphinato manganese
PFe = Porphinato iron
PCo = Porphinato cobalt

TABLE 2

| No. | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ | $R^{13}$ | $R^{14}$ | $R^{15}$ | $R^{16}$ | M | Name |
|---|---|---|---|---|---|---|---|---|---|---|---|---|---|---|---|---|---|---|
| 1 | H | H | H | H | H | H | H | H | H | H | H | H | H | H | H | H | Mn | FC - Manganese |
| 2 | " | " | " | " | " | " | " | " | " | " | " | " | " | " | " | " | Fe | FC - Iron |
| 3 | " | " | " | " | " | " | " | " | " | " | " | " | " | " | " | " | Co | FC - Cobalt |
| 4 | " | " | " | " | " | " | " | " | " | " | " | " | " | " | " | " | Cu | FC - Copper |
| 5 | Cl | Cl | Cl | Cl | Cl | Cl | Cl | Cl | Cl | Cl | Cl | Cl | Cl | Cl | Cl | Cl | Cu | Hexadecachloro FC - copper |
| 6 | " | " | " | " | " | " | " | " | " | " | " | " | " | " | " | " | Fe | Hexadecachloro FC - iron |
| 7 | Br | Br | Br | Br | Br | Br | Br | Br | Br | Br | Br | Br | Br | Br | Br | Br | Cu | Hexadecabromo FC - copper |
| 8 | F | F | F | F | F | F | F | F | F | F | F | F | F | F | F | F | Co | Hexadecafluoro FC - cobalt |
| 9 | " | " | " | " | " | " | " | " | " | " | " | " | " | " | " | " | Fe | Hexadecafluoro FC - iron |

Note FC = Phthalocyanine

The preparation of the organometallic complex catalyst is known. The porphyrin metal complex catalyst can be prepared easily, for example, by a process (J. Am. Chem. Coc., 81, 5111, 1959) wherein an organic acid is refluxed in the presence of porphyrin and a metal salt; a process (J. Inorg. Nucl. Chem., 32, 2443, 1970) wherein dimethyl formamide is refluxed in the presence of porphyrin and a metal salt; or a process (Justus Liebigs Ann. Chem., 745, 135, 1971) wherein an organic solvent such as benzene, chloroform or phenol is refluxed in the presence of porphyrin and metal acetyl acetonate. As known well, porphyrin can be prepared easily by the reaction of pyrroles (e.g.

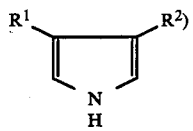

and aldehydes (e.g. $X_1CHO$). The phthalocyanine metal complex catalyst can be prepared easily by a process (J. Chem. Soc., 1157, 1938) wherein anhydrous metal salt and phthalocyaninedilithium are reacted in ethanol at room temperature. The amount of the organometallic complex catalyst to be used in practising the process of the present invention is preferably in the range of $10^{-6}$ mole to 0.2 mole, more preferably $10^{-5}$ mole to 0.05 mole, per 1 mole of $\beta$-isophorone. Even molar ratios outside this range may be adopted as long as they are not an obstacle to the reaction selectivity. The reaction is performed in the presence of an organic base. As the organic base an alkylamine (mono-, di- or trialkylamine wherein the alkyl preferably has 1 to 8 carbon atoms) is preferred. Examples, which are particularly preferred, are secondary and tertiary amines, such as dimethylamine, trimethylamine, diethylamine, methyl ethyl amine, triethylamine, dibutylamine, diisopropylamine and ethyl butyl amine. The amount of the organic base to be used is preferably in the range of 0.02 to 20 moles, more preferably 0.1 to 5 moles, per 1 mole of $\beta$-isophorone. Although the reaction can be carried out in the presence of the organic base alone, it is preferably conducted in the presence of both the organic base and a solvent. As examples of the reaction solvent there are mentioned hydrocarbon solvents such as hexane, benzene, toluene and xylene; ether solvents such as diethyl ether, diisopropyl ether, dibutyl ether, tetrahydrofuran, dioxane, ethylene glycol dimethyl ether, ethylene glycol monomethyl ether, diethylene glycol dimethyl ether, diethylene glycol monomethyl ether, tetrahydropyran and dioxane; ketone solvents such as acetone, methyl isobutyl ketone, methyl ethyl ketone and methyl butyl ketone; halogen solvents such as monochloroethane, dichloromethane, chloroform, carbon tetrachloride and 1,2-dichloroethane; alcohol solvents such as methanol, ethanol, butanol and propanol; carboxamide solvents such as dimethylformamide, dimethylacetamide, diethylformamide and N-methylpyrrolidone; nitrile solvents such as acetonitrile, propionitrile and butyronitrile; ester solvents such as methyl acetate, ethyl acetate and butyl acetate; water; $\alpha$-isophorone; and optional mixtures thereof. The addition of water is effective in increasing the conversion rate of $\beta$-isophorone. The reaction time is preferably in the range of 0.1 to 60 hours, more preferably 0.5 to 20 hours, and the reaction temperature is preferably in the range of $-30°$ to $80°$ C., more preferably $0°$ to $50°$ C. The reaction can be carried out at atmospheric pressure or under the application of pressure.

Then, the solvent and the organic base are recovered under reduced pressure, followed by reduced-pressure distillation or steam distillation, or the reaction solution is filtered and the filtrate is poured into an excess amount of a peroxide deactivator such as an aqueous sodium sulfite solution, an aqueous ferric sulfate solution or an aqueous ferric chloride solution, followed by extraction using a suitable extraction solvent such as, for example, ethyl acetate, benzene, toluene, diethyl ether, carbon tetrachloride, chloroform, or dichloroethane, then the solvent layer is washed with saturated sodium hydrogencarbonate or saturated aqueous NaCl, followed by drying using a desiccant, e.g. magnesium sulfate, and the solvent is recovered by distillation to obtain 3,5,5-triethylcyclohexa-2-en-1,4-dione, which may be purified, if necessary, by such means as reduced-pressure distillation, column chromatography, or recrystallization.

The present invention will be described by the following Examples.

EXAMPLE 1

502 mg ($3.63 \times 10^{-3}$ mole) of $\beta$-isophorone, 4.4 ml of ethylene glycol dimethyl ether, 143 mg ($1.41 \times 10^{-3}$ mole) of triethylamine and 37 mg ($6.52 \times 10^{-5}$ mole) of phthalocyanine manganese were placed and mixed in a 10 ml flask equipped with a thermometer, a stirrer and an oxygen introducer, and the vapor phase portion in the flask was purged with oxygen. Stirring was started and reaction was allowed to proceed while introducing oxygen gas corresponding to that consumed in the reaction, into the vapor phase portion at atmospheric pressure under control of the reaction temperature at $30°$ C. After stirring for 4 hours, the reaction solution was filtered using Celite, then ethylene glycol diethyl ether and triethylamine were recovered from the filtrate under reduced pressure to obtain 589 mg of a liquid residue. A quantitative analysis of the liquid residue established that it contained 71.3 wt.% of 3,5,5-trimethylcyclohexa-2-en-1,4-dione. (Reaction yield: 75.0 mol%).

EXAMPLE 2

499 mg ($3.61 \times 10^{-3}$ mole) of β-isophorone, 4.4 ml of dimethylformamide, 143 mg ($1.41 \times 10^{-3}$ mole) of triethylamine and 37 mg ($6.52 \times 10^{-5}$ mole) of phthalocyanine manganese were placed and mixed in the reactor described in Example 1 and the vapor phase portion in the flask was purged with oxygen, followed by the same reaction operation as in Example 1. After stirring at 30° C. for 3 hours, the reaction solution was filtered using Celite, then triethylamine and dimethylformamide were recovered from the filtrate under reduced pressure to obtain 631 mg of a liquid residue. As a result of quantitative analysis by gas chromatography the liquid residue was found to contain 69.4 wt.% of 3,5,5-trimethylcyclohexa-2-en-1,4-dione. (Reaction yield: 78.7 mole%)

EXAMPLE 3

500 ml ($3.62 \times 10^{-3}$ mole) of β-isophorone, 4.4 ml of dimethylformamide, 145 mg ($1.43 \times 10^{-3}$ mole) of triethylamine and 7.5 mg ($1.32 \times 10^{-5}$ mole) of phthalocyanine manganese were placed and mixed in the reactor described in Example 1 and the vapor phase portion in the flask was purged with oxygen, followed by the same reaction operation as in Example 1. After stirring at 30° C. for 6.5 hours, triethylamine and dimethylformamide were recovered under reduced pressure to obtain 645 mg of a liquid residue. As a result of quantitative analysis by gas chromatography, the liquid residue was found to contain 67.8 wt.% of 3,5,5-trimethylcyclohexa-2-en-1,4-dione. (Reaction yield: 78.4 mol%)

EXAMPLE 4

501 mg ($3.62 \times 10^{-3}$ mole) of β-isophorone, 149 mg ($1.49 \times 10^{-3}$ mole) of triethylamine, 0.16 ml of ethyl acetate, 4.4 ml of ethylene glycol dimethyl ether and 75 mg ($1.32 \times 10^{-4}$ mole) or phthalocyanine iron were placed and mixed in the reactor described in Example 1 and the vapor phase portion in the flask was purged with oxygen, followed by the same reaction operation as in Example 1. After stirring at 30° C. for 6.7 hours, the reaction solution was filtered using Celite, then ethylene glycol dimethyl ether, triethylamine and ethyl acetate were recovered from the filtrate under reduced pressure to obtain 549 mg of a liquid residue. As a result of quantitative analysis by gas chromatography, the liquid residue was found to contain 80.0 wt.% of 3,5,5-trimethylcyclohexa-2-en-1,4-dione. (Reaction yield: 78.6 mole%)

EXAMPLE 5

505 mg ($3.65 \times 10^{-3}$ mole) of β-isophorone, 140 mg ($1.38 \times 10^{-3}$ mole) of triethylamine, 176 mg of water, 4.4 ml of ethylene glycol dimethyl ether and 29 mg ($5.10 \times 10^{-5}$ mole) of phthalocyanine iron were placed and mixed in the reactor described in Example 1 and the vapor phase portion in the flask were purged with oxygen, followed by the same reaction operation as in Example 1. After stirring at 30° C. for 8 hours, the reaction solution was filtered using Celite, then ethylene glycol dimethyl ether and triethylamine were recovered from the filtrate at reduced pressure to obtain 569 mg of a liquid residue. As a result of quantitative analysis by gas chromatography, the liquid residue was found to contain 73.8 wt.% of 3,5,5-trimethylcyclohexa-2-en-1,4-dione. (Reaction yield: 74.5 mole%)

EXAMPLE 6

500 mg ($3.61 \times 10^{-3}$ mole) of β-isophorone, 143 mg ($1.41 \times 10^{-3}$ mole) of triethylamine, 176 mg of water, 4.4 ml of ethylene glycol dimethyl ether and 75 mg ($1.31 \times 10^{-4}$ mole) of phthalocyanine cobalt were placed and mixed in the reactor described in Example 1 and the vapor phase portion in the flask was purged with oxygen, followed by the same reaction operation as in Example 1. After stirring at 30° C. for 6.5 hours, the reaction solution was filtered using Celite, then ethylene glycol dimethyl ether and triethylamine were recovered at reduced pressure to obtain 621 mg of a liquid residue. As a result of quantitative analysis by gas chromatography the liquid residue was found to contain 52.0 wt.% of 3,5,5-trimethylcyclohexa-2-en-1,4-dione. (Reaction yield: 57.9 mole%)

EXAMPLE 7

500 mg ($3.61 \times 10^{-3}$ mole) of β-isophorone, 143 mg ($1.41 \times 10^{-3}$ mole) of triethylamine, 0.16 ml of ethyl acetate, 4.4 ml of ethylene glycol dimethyl ether and 75 mg ($6.65 \times 10^{-5}$ mole) of 1,2,3,4,8,9,10,11,15,16,17,18,22,23,24,25-hexadecachlorophthalocyanine copper were placed and mixed in the reactor described in Example 1 and the vapor phase portion in the flask was purged with oxygen, followed by the same reaction operation as in Example 1. After stirring at 30° C. for 6.5 hours, the reaction solution was filtered using Celite, then ethyl acetate, ethylene glycol dimethyl ether and triethylamine were recovered from the filtrate at reduced pressure to obtain 595 mg of a liquid residue. As a result of quantitative analysis by gas chromatography, the liquid residue was found to contain 63.1 wt.% of 3,5,5-trimethylcyclohexa-2-en-1,4-dione. (Reaction yield: 67.3 mole%)

EXAMPLE 8

500 mg ($3.61 \times 10^{-3}$ mole) of β-isophorone, 143 mg ($1.41 \times 10^{-3}$ mole) of triethylamine, 176 mg of water, 4.4 ml of ethylene glycol dimethyl ether and 75 mg ($6.65 \times 10^{-5}$ mole) of 1,2,3,4,8,9,10,11,15,16,17,18,22,23,24,25-hexadecachlorophthalocyanine copper were placed and mixed in the reactor described in Example 1 and the vapor phase portion in the flask was purged with oxygen, followed by the same reaction operation as in Example 1. After stirring at 30° C. for 5 hours, the reaction solution was filtered using Celite, then triethylamine and ethylene glycol dimethyl ether were recovered from the filtrate at reduced pressure to obtain 675 mg of a liquid residue. As a result of quantitative analysis by gas chromatography, the liquid residue was found to contain 58.2 wt.% of 3,5,5-trimethylcyclohexa-2-en-1,4-dione. (Reaction yield: 70.4 mole%)

EXAMPLE 9

501 mg ($2.62 \times 10^{-3}$ mole) of β-isophorone, 143 mg ($1.41 \times 10^{-3}$ mole) or triethylamine, 4.4 ml of ethylene glycol dimethyl ether and 7.5 mg ($1.07 \times 10^{-5}$ mole) of chloro-5,10,15,20-tetraphenyl porphyrinato manganese were placed and mixed in the reactor described in Example 1 and the vapor phase portion in the flask was purged with oxygen, followed by the same operation as in Example 1. After stirring at 30° C. for 4 hours, ethylene glycol dimethyl ether and triethylamine were recovered from the reaction solution at reduced pressure to obtain 592 mg of a liquid residue. As a result of quantitative analysis by gas chromatography, the liquid residue was found to contain 88.8 wt.% of 3,5,5-trimethylcyclohexa-2-en-1,4-dione. (Reaction yield: 94.0 mole%)

EXAMPLE 10

1,001 mg ($7.24 \times 10^{-3}$ mole) of β-isophorone, 285 mg ($2.82 \times 10^{-3}$ mole) of triethylamine, 366 mg of water, 8.8 ml of ethylane glycol dimethyl ether and 2.0 mg ($2.84 \times 10^{-6}$ mole) of chloro-5,10,15,20-tetraphenyl porphyrinato manganese were placed and mixed in a 20 ml flask equipped with a thermometer, a stirrer and an oxygen introducer and the vapor phase portion in the flask was purged with oxygen, followed by the same reaction operation as in Example 1. After stirring at 30° C. for 1.5 hours, ethylene glycol dimethyl ether and triethylamine were recovered from the reaction solution at reduced pressure to obtain 1,312 mg of a liquid residue. As a result of quantitative analysis by gas chromatography, the liquid residue was found to contain 82.1 wt.% of 3,5,5-trimethylcyclohexa-2-en-1,4-dione. (Reaction yield: 96.4 mole%)

EXAMPLE 11

1,000 mg ($7.24 \times 10^{-3}$ mole) of β-isophorone, 287 mg ($2.84 \times 10^{-3}$ mole) of triethylamine, 356 mg of water, 8.8 ml of ethylene glycol dimethyl ether, 1.0 ml of methylene chloride and 2.0 mg ($1.84 \times 10^{-6}$ mole) of 5,10,15,20-tetraphenyl porphyrinato manganese were placed and mixed in the reactor described in Example 10 and the vapor phase portion in the flask was purged with oxygen, followed by the same reaction operation as in Example 1. After stirring at 30° C. for 2.5 hours, ethylene glycol dimethyl ether and triethylamine were recovered from the filtrate at reduced pressure to obtain 1,329 mg of a liquid residue. As a result of quantitative analysis by gas chromatography, the liquid residue was found to contain 82.3 wt.% of 3,5,5-trimethylcyclohexa-2-en-1,4-dione. (Reaction yield: 98.0 mole%)

EXAMPLE 12

500 mg ($3.62 \times 10^{-3}$ mole) of β-isophorone, 144 mg ($1.42 \times 10^{-3}$ mole) of triethylamine, 4.4 ml of ethylene glycol dimethyl ether and 75 mg ($1.12 \times 10^{-4}$ mole) of 5,10,15,20-tetraphenyl porphyrinato cobalt were placed and mixed in the reactor described in Example 1 and the vapor phase portion in the flask was purged with oxygen, followed by the same reaction operation as in Example 1. After stirring at 30° C. for 6.5 hours, the reaction solution was filtered using Celite, then ethylene glycol dimethyl ether and triethylamine were recovered from the filtrate at reduced pressure to obtain 559 mg of a liquid residue. As a result of quantitative analysis by gas chromatography, the liquid residue was found to contain 72.4 wt.% of 3,5,5-trimethylcyclohexa-2-en-1,4-dione. (Reaction yield: 72.5 mole%)

EXAMPLE 13

500 mg ($3.62 \times 10^{-3}$ mole) of β-isophorone, 144 mg ($1.42 \times 10^{-3}$ mole) of triethylamine, 0.16 ml of ethyl acetate, 4.4 ml of ethylene glycol dimethyl ether and 66 mg ($9.33 \times 10^{-5}$ mole) of chloro-5,10,15,20-tetraphenyl porphyrinato cobalt were placed and mixed in the reactor described in Example 1 and the vapor phase portion in the flask was purged with oxygen, followed by the same reaction operation as in Example 1. After stirring at 30° C. for 6.5 hours, the reaction solution was filtered using Celite, then ethylene glycol dimethyl ether and triethylamine were recovered from the filtrate at reduced pressure to obtain 569 mg of a liquid residue. As a result of quantitative analysis by gas chromatography, the liquid residue was found to contain 78.0 wt.% of 3,5,5-trimethylcyclohexa-2-en-1,4-dione. (Reaction yield: 79.6 mole%)

EXAMPLE 14

499 mg ($3.61 \times 10^{-3}$ mole) of β-isophorone, 148 mg ($1.46 \times 10^{-3}$ mole) or triethylamine, 0.16 ml of ethyl acetate, 4.4 ml of ethylene glycol dimethyl ether and 75 mg ($1.07 \times 10^{-4}$ mole) of chloro-5,10,15,20-tetraphenyl porphyrinato iron were placed and mixed in the reactor described in Example 1 and the vapor phase portion in the flask was purged with oxygen, followed by the same reaction operation as in Example 1. After stirring at 30° C. for 6.5 hours, the reaction solution was filtered using Celite, then ethylene glycol dimethyl ether and triethylamine were recovered from the filtrate at reduced pressure to obtain 532 mg of a liquid residue. As a result of quantitative analysis by gas chromatography, the liquid residue was found to contain 50.7 wt.% of 3,5,5-trimethylcyclohexa-2-en-1,4-dione. (Reaction yield: 48.4 mole%)

What is claimed is:

1. A process for preparing 3,5,5-trimethylcyclohexa-2-en-1,4-dione comprising oxidizing 3,5,5-trimethylcyclohexa-3-en-one with molecular oxygen or a molecular oxygen-containing gas in the presence of an alkylamine and an organometallic complex catalyst selected from the group consisting of a porphyrin complex of manganese, cobalt, iron or copper, a substituted porphyrin complex of manganese, cobalt, iron or copper, a phthalocyanine complex of manganese, cobalt, iron or copper and a substituted phthalocyanine complex of manganese, cobalt, iron or copper.

2. A process as set forth in claim 1, wherein said organometallic complex catalyst is a porphyrin complex of manganese or cobalt.

3. A process as set forth in claim 1, wherein said organometallic complex catalyst is a phthalocyanine complex of manganese or iron.

4. A process as set forth in claim 1, wherein said alkylamine is a di- or trialkylamine.

5. A process as set forth in claim 1, wherein said organometallic complex catalyst is used in an amount of $10^{-6}$ mole to 0.2 mole per mole of the 3,5,5-trimethylcyclohexa-3-en-1-one.

6. A process as set forth in claim 1, wherein said alkylamine is used in an amount of 0.02 to 20 moles per mole of the 3,5,5-trimethylcyclohexa-3-en-1-one.

7. A process as set forth in claim 1, wherein the reaction temperature is in the range of −30° C. to 80° C.

8. A process as set forth in claim 1, wherein said organometallic complex catalyst is selected from the group consisting of a porphyrin complex of manganese and a phthalocyanine complex of manganese.

9. A process as set forth in claim 1, wherein said substituted porphyrin complex has the structural formula

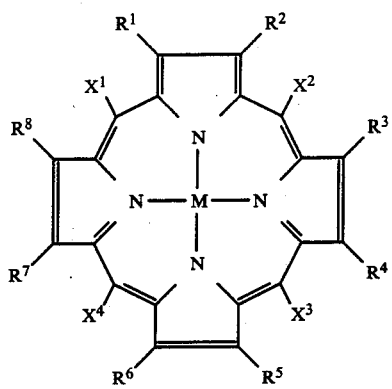

where $X^1$, $X^2$, $X^3$ and $X^4$ are the same or different and are hydrogen, $C_1$–$C_4$ alkyl, $C_1$–$C_4$ alkoxy, phenyl or phenyl substituted with 1 to 5 halogen atoms, $C_1$–$C_4$ alkyl, $C_1$–$C_4$ alkoxy or phenyl; $R^1$, $R^2$, $R^3$, $R^4$, $R^5$, $R^6$, $R^7$ and $R^8$ are each hydrogen, $C_1$–$C_4$ alkyl, $C_1$–$C_4$ alkoxy, halogen, $C_1$–$C_4$ alkylamino or nitro; and M is manganese, cobalt, iron or copper with the proviso that if $R^1$, $R^2$, $R^3$, $R^4$, $R^5$, $R^6$, $R^7$ and $R^8$ are each hydrogen then at least one of $X^1$, $X^2$, $X^3$ and $X^4$ is not hydrogen.

10. A process as set forth in claim 1, wherein said substituted phthalocyanine complex has the structural formula

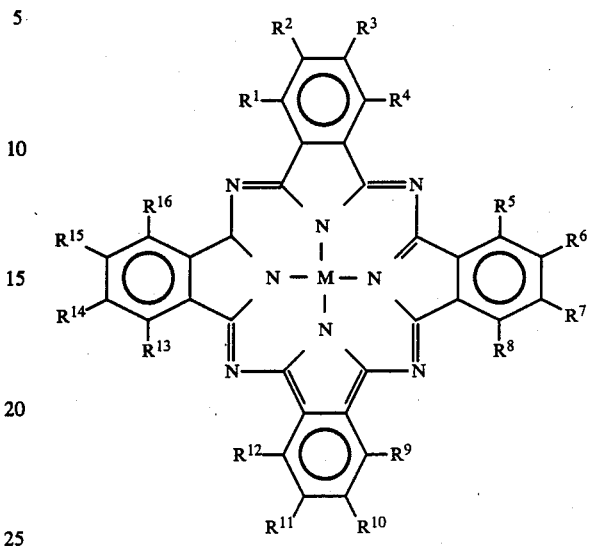

where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ are each $C_1$–$C_4$ alkyl, $C_1$–$C_4$ alkoxy, halogen or $C_1$–$C_4$ alkylamino; and M is manganese, iron, cobalt or copper.

* * * * *